United States Patent
Whitehurst et al.

(10) Patent No.: US 6,885,895 B1
(45) Date of Patent: Apr. 26, 2005

(54) METHODS AND SYSTEMS FOR ELECTRICAL AND/OR DRUG STIMULATION AS A THERAPY FOR ERECTILE DYSFUNCTION

(75) Inventors: Todd K. Whitehurst, Santa Clarita, CA (US); James P. McGivern, Stevenson Ranch, CA (US)

(73) Assignee: Advanced Bionics Corporation, Valencia, CA (US)

( * ) Notice: Subject to any disclaimer, the term of this patent is extended or adjusted under 35 U.S.C. 154(b) by 557 days.

(21) Appl. No.: 10/119,561

(22) Filed: Apr. 9, 2002

Related U.S. Application Data

(60) Provisional application No. 60/286,744, filed on Apr. 26, 2001.

(51) Int. Cl.[7] ................................................ A61N 1/08
(52) U.S. Cl. ................................................ 607/39
(58) Field of Search .................... 607/2, 39, 40, 607/72; 604/21; 514/573, 645; 128/898, 899

(56) References Cited

U.S. PATENT DOCUMENTS

| | | | |
|---|---|---|---|
| 3,941,136 A | 3/1976 | Bucalo | 128/422 |
| 4,542,753 A | 9/1985 | Brenman et al. | 128/788 |
| 4,585,005 A | 4/1986 | Lue et al. | 128/419 |
| 5,193,539 A | 3/1993 | Schulman et al. | 128/419 |
| 5,193,540 A | 3/1993 | Schulman et al. | 128/419 |
| 5,312,439 A | 5/1994 | Loeb | 607/2 |
| 5,324,316 A | 6/1994 | Schulman et al. | 607/61 |
| 5,405,367 A | 4/1995 | Schulman et al. | 607/61 |
| 5,439,938 A | 8/1995 | Snyder et al. | 514/565 |
| 5,454,840 A | 10/1995 | Krakovsky et al. | 607/39 |
| 5,571,118 A | 11/1996 | Boutos | 607/138 |
| 5,594,032 A * | 1/1997 | Gonzalez-Cadavid et al. | 514/645 |
| 5,775,331 A | 7/1998 | Raymond et al. | 128/741 |
| 5,807,306 A * | 9/1998 | Shapland et al. | 604/21 |
| 5,938,584 A | 8/1999 | Ardito et al. | 600/38 |
| 6,051,017 A | 4/2000 | Loeb et al. | 607/1 |
| 6,169,924 B1 | 1/2001 | Meloy et al. | 607/39 |
| 6,642,274 B1 * | 11/2003 | Neal | 514/573 |
| 6,650,943 B1 * | 11/2003 | Whitehurst et al. | 607/39 |
| 2003/0018365 A1 * | 1/2003 | Loeb | 607/40 |

FOREIGN PATENT DOCUMENTS

| | | |
|---|---|---|
| WO | 9837926 | 3/1998 |
| WO | 9843700 | 8/1998 |
| WO | 9843701 | 8/1998 |

OTHER PUBLICATIONS

Cameron, et al., "Micromodular Implants to Provide Electrical Stimulation of Paralyzed Muscles and Limbs", IEEE Transactions on Biomedical Engineering, vol. 44, No. 9 (Sep. 1997), pp. 781–790.

Lue, et al., "Electrostimulation and Penile Erection", Urol. Int. 40 (1985), pp. 60–64.

(Continued)

*Primary Examiner*—George Manuel
(74) *Attorney, Agent, or Firm*—Laura Haburay Bishop

(57) ABSTRACT

Systems and methods for introducing one or more stimulating drugs and/or applying electrical stimulation to tissue affecting the penis to treat erectile dysfunction (for instance, following prostate surgery) uses at least one implantable system control unit (SCU) producing electrical pulses delivered via electrodes and/or producing drug infusion pulses, wherein the stimulating drug(s) are delivered via one or more pumps and infusion outlets.

26 Claims, 8 Drawing Sheets

OTHER PUBLICATIONS

Martinez–Pineiro, et al., Rat Model for the Study of Penile Erection: Pharmacologic and Electrical–Stimulation Parameters, Eur Urol 25 (1994), pp. 62–70.

Shafik, A., "Extrapelvic Cavernous Nerve Stimulation in Erectile Dysfunction", Andrologia 28 (May–Jun. 1996), pp. 151–156.

Stief, et al., "The Influence of Anterior Root Stimulation (S2) in Deafferented Spinal Cord Injury Men on Cavernous Electrical Activity", The Journal of Urology 148 (Jul. 1992), pp. 107–110.

Tai, et al., "Penile Erection Produced by Microstimulation of the Sacral Spinal Cord of the Cat", IEEE Transactions Rehabilitation Engineering 6 (Dec. 1998) pp. 374–381.

Shafik A., "Perineal Nerve Stimulation: Role in Penile Erection", International Journal of Impotence Research. 9 (Mar. 1997), pp. 11–16.

Shafik A., "Cavernous Nerve Stimulation Through an Extrapelvic Subpubic Approach: Role in Penile Erection", Eur Urol 26 (1994), pp. 98–102.

Creasey GH., "Electrical Stimulation of Sacral Roots for Micturition After Spinal Cord Injury", Urologic Clinics of North America 20 (Aug. 1993), pp. 505–515.

Allen, T., "The Effects of Viagra on the Action of Nitric Oxide", Emory's Center for Interactive Teaching (ECIT), Emory University, http://www.ecit.emory.edu/ECIT/chem_ram/viag/viagra2.htm.

Ballard, et al., "Effects of Sildenafil on the Relaxation of Human Corpus Cavernosum Tissue in Vitro and on the Activities of Cyclic Nucleotide Phosphodiesterase Isozymes". The Journal of Urology 159 (1996), pp. 2164–2171.

Carter, et al., "Effect of the Selective Phosphodiesterase Type Inhibitor Sildenafil on Erectile Function in the Anesthetized Dog", The Journal of Urology 160 (1998), pp. 242–246.

Goldstein, et al., "Oral Sildenafil in the Treatment of Erectile Dysfunction", The New England Journal of Medicine 338 (1998), pp. 1397–1404.

Moreland, et al. "Sildenafil, a Novel Inhibitor of Phosphodiesterase Type 5 in Human Corpus Cavernosum Smooth Muscle Cells", Life Sciences 62 (1998), pp. 309–318.

Kim, et al., "Alpha–Adrenergic Receptor Blockade by Phentolamine Increases the Efficacy of Vasodilators in Penile Corpus Cavernosum", Int J Impot Res, vol. 12, Supp 1, (Mar. 2000), pp. 26–36.

Stanford, et al., "Urinary and Sexual Function After Radical Prostatectomy for Clinically Localized Prostate Cancer— The Prostate Cancer Outcomes Study", The journal of the American Medical Association (JAMA) 19 (Jan. 2000), pp. 354–360.

Annich, et al., "Reduced Platelet Activation and Thrombosis in Extracorporeal Circuits Coated with Nitric Oxide Release Polymers", Crit Care Med, 28 (Apr. 2000), pp. 915–920.

Mowery, et al., "Preparation and Characterization of Hydrophobic Polymeric Films that are Thromboresistant Via Nitric Oxide Release", Biomaterials 21 (Jan. 2000), pp. 9–21.

AB–124U; Whitehurst and McGivern, inventors; U.S. Appl. No. 09/799,988; filed Mar. 6, 2001; entitled "Fully Implantable Neurostimulator for Cavernous Nerve Stimulation as a Therapy for Erectile Dysfunction and Other Sexual Dysfuntion".

AB–124U1; Whitehurst and McGivern, inventors; U.S. Appl. No. 09/927,757; filed Aug. 9, 2001; entitled "Spinal Cord Stimulation as a Therapy for Sexual Dysfuntion".

* cited by examiner

METHODS AND SYSTEMS FOR ELECTRICAL AND/OR DRUG STIMULATION AS A THERAPY FOR ERECTILE DYSFUNCTION

The present application claims the benefit of U.S. Provisional Patent Application Ser. No. 60/286,744, filed Apr. 26, 2001, which application is incorporated herein by reference in its entirety.

FIELD OF THE INVENTION

The present invention relates to implantable drug delivery and electrical stimulation systems and methods, and more particularly relates to utilizing one or more implantable devices to deliver electrical stimulation and/or one or more stimulating drugs as a therapy for erectile dysfunction, for instance, following prostatic surgery.

BACKGROUND OF THE INVENTION

Recent estimates suggest that the number of U.S. men with erectile dysfunction may be near 10 to 20 million, and inclusion of individuals with partial erectile dysfunction increases the estimate to about 30 million. Erectile dysfunction has a number of etiologies, including neuropathy and vascular disease. The male erectile response is initiated by the action of neurons, or nerve cells (i.e., neuronal action), and is maintained by a complex interplay between events involving blood vessels (i.e., vascular events) and events involving the nervous system (i.e., neurological events).

The part of the nervous system that regulates involuntary action (e.g., the intestines, heart, glands) is the autonomic nervous system. The autonomic nervous system is divided into two mutually antagonistic, physiologically and anatomically distinct systems: the sympathetic nervous system and the parasympathetic nervous system. The sympathetic nervous system originates in the thoracic and lumbar regions of the spinal cord, and in general, opposes the physiological affects of the parasympathetic nervous system. For instance, the sympathetic system tends to reduce digestive secretions or speed up the heart, usually when an individual is in an active state. The parasympathetic nervous system originates in the brain stem and the lower part of the spinal cord, and, in general, opposes the physiological effects of the sympathetic nervous system. Thus, the parasympathetic nervous system tends to stimulate digestive secretions or slow the heart, usually when an individual is in a relaxed state.

It is parasympathetic neuronal action that initiates the male erectile response. Specifically, this parasympathetic input originates from the pelvic splanchnic nerve plexus. The pelvic splanchnic nerve plexus is comprised of branches from the second, third, and fourth sacral nerves (from the lower part of the spinal cord) that intertwine with the inferior hypogastric plexus, which is a network of nerves in the pelvis. The cavernous nerves (designated greater and lesser) are derived from the pelvic splanchnic nerves, via the prostatic plexus, and supply parasympathetic fibers to the corpora cavernosa and corpus spongiosum, the spongy tissues in the penis that are engorged with blood during an erection. The corpora cavernosa are two paired tissue bodies that lie dorsally in the penis, while the corpus spongiosum is located ventrally and surrounds the urethra. The corpus spongiosum expands at the terminal end to form the glans penis. These erectile tissues are composed of venous spaces lined with epithelial cells separated by connective tissue and smooth muscle cells.

Parasympathetic activity allows erection by relaxation of the smooth muscle (i.e., muscle found in the walls of internal organs, blood vessels, hair follicles, etc. that contracts without voluntary control) and dilation of the helicine arteries, which are arteries found in the erectile tissue of the penis. The dilation of the arteries causes greatly increased blood flow through the erectile tissue, which leads to expansion of the corpora cavernosa and the corpus spongiosum. As the corpora cavernosa and the corpus spongiosum expand, the venous structures draining the penis are compressed against the fascia surrounding each of the erectile tissues (i.e., the tunica albuginea of the corpora cavernosa and the tunica albuginea of the corpus spongiosum). Thus, the outflow of blood is restricted, and the internal pressure increases. This vein-obstruction process is referred to as the corporal veno-occlusive mechanism.

Conversely, sympathetic innervation from the hypogastric nerves and/or certain nerves of the inferior hypogastric plexus, which derive from the sympathetic ganglia, inhibit parasympathetic activity and cause constriction of the smooth muscle and helicine arteries, making the penis flaccid. The flaccid state is maintained by continuous sympathetic (alpha-adrenergic) nervous system stimulation of the penile blood vessels and smooth muscle.

Erectile dysfunction has a number of causes, both physiological and psychological, and in many patients the disorder may be multifactorial. The causes include several that are essentially neurologic in origin. Damage to the spinal cord may produce varying degrees of erectile failure depending on the location and severity of the damage. Damage to the pathways used by the autonomic nervous system to innervate the penis may interrupt "psychogenic" erection initiated by the central nervous system. Damage to somatic nervous pathways may impair reflexogenic erections and may interrupt tactile sensation needed to maintain psychogenic erections. Not only do traumatic lesions affect erectile ability, but disorders leading to peripheral neuropathy may impair neuronal innervation of the penis or of the sensory afferents. The endocrine system itself, particularly the production of androgens, appears to play a role in regulating sexual interest, and may also play a role in erectile function.

Erectile dysfunction is a common complication of prostate surgery, such as prostatectomy (surgical removal of all or part of the prostate), which is a mainstay of treatment for prostate cancer. Approximately 180,000 new cases of prostate cancer will occur in the US each year, with 35,000 men expected to die of the disease annually. A January 2000 study of 1,042 men diagnosed with primary prostate cancer and who underwent radical prostatectomy for localized prostate cancer showed that at least 18 months following surgery, 59.9 percent were impotent and 8.4 percent were incontinent. At 24 months, 59.9 percent of men reported that erections were not firm enough for sexual intercourse, and 44.2 percent were unable to have any erections.

Among men who were not impotent before surgery, the proportion of men who reported being impotent 18 or more months after surgery varied according to whether a nerve-sparing procedure was attempted. Nerve-sparing procedures attempt to leave intact one or both of the "neurovascular bundles" which pass close to the prostate capsule. In most cases, the "bundles" are essential for achieving and maintaining an erection. In the January 2000 study, 65.6 percent of non-nerve-sparing, 58.6 percent of unilateral nerve-sparing, and 56.0 percent of bilateral nerve-sparing procedures produced impotence. Despite the level of urinary incontinence and sexual dysfunction reported in this study, most men (71.5 percent) reported they would choose radical prostatectomy again.

To achieve improved outcomes in nerve-sparing surgery, devices are available for intra-operative cavernous nerve simulation, often with penile tumescence monitoring. The UroMed CaverMap™ Surgical Aid is an example of such a device. The CaverMap™ is an acute neurostimulator used to stimulate the cavernous nerves during prostate surgery. Upon such stimulation, the penis becomes erect within 20 seconds to 1 minute. During a typical procedure, the CaverMap™ Surgical Aid is used initially to establish the baseline erectile response to stimulation via stimulation bilaterally at the posterolateral urethra. As the surgery progresses and the neurovascular bundle is visualized, the CaverMap™ is used to stimulate bilaterally along the lateral pedicles at the apex, mid, and base of prostate. Part or all of the prostate and seminal vesicles are removed, sparing those portions containing the cavernous nerves.

There are few good options for men suffering from erectile dysfunction following prostatic surgery. A well-publicized oral medication, sildenafil citrate (available from Pfizer Inc. of New York, N.Y.) under the trademarked name Viagra®, is available, but requires an hour to exert its full effects, and may have significant side effects such as abnormal vision, flushing, headache, and diarrhea. Vardenafil is a medication undergoing clinical investigation, which has a mechanism of action similar to sildenafil. Despite its drawbacks, the ability to preserve erectile function following prostate surgery has been favorably affected by the availability of sildenafil. Sildenafil appears to be most effective when there is some remaining erectile function.

Intracavernosal injection therapy, in which a patient injects vasodilator substances (e.g., alprostadil, papaverine, phentolamine) into the corpora of the penis, suffers a high rate of patient dropout. The most commonly used drug is alprostadil. Alprostadil is naturally occurring prostaglandin $E_1$, or $PGE_1$, that is present in the penis and is involved in the natural erection process. (Thus, "alprostadil", "prostaglandin $E_1$", and "$PGE_1$" are used interchangeable herein.) Alprostadil has been used in the treatment of impotence in the UK since 1994. Alprostadil relaxes the blood vessels and muscles in the erectile tissue of the penis allowing increased blood flow, the basis of a normal erection.

Intracavernosal injection therapy suffers a high rate of patient dropout, as does the therapeutic application of vacuum constriction devices. Several forms of penile prostheses are available, including semirigid, malleable, and inflatable, but these have significant problems with mechanical failure, infection, and device erosion. As has been shown, various stimulation devices and medications have been proposed for treating erectile dysfunction, most with significant drawbacks.

SUMMARY OF THE INVENTION

The invention disclosed and claimed herein provides, inter alia, means for implanting electrode(s) and/or catheters during prostate surgery. If stimulation is not needed to aid erectile function, the lead(s)/catheter(s) may be removed or may alternatively remain in the body. If the patient experiences erectile dysfunction, however, the lead(s)/catheter(s) are used to stimulate certain structures, such as the cavernous nerves, to determine the efficacy of electrical and/or drug stimulation. In patients who respond favorably, chronic stimulation means may then be implanted.

Systems and methods of the present invention provide the application of a stimulating drug(s) alone or in combination with electrical stimulation. Drug stimulation of specific sites innervating and/or within the penis and surrounding areas may have significant therapeutic benefit in restoring the patient's erectile function. For instance, infusing substances into the penis and/or its arterial supply may provide effective therapy. Additional uses of the present invention include application to emission (discharge of semen) and ejaculation (ejection of semen in orgasm).

The invention is carried out via one or more system control units (SCUs) that apply electrical stimulation and/or one or more stimulating drugs to one or more predetermined stimulation sites. In some forms of SCUs, one or more electrodes are surgically implanted to provide electrical stimulation from an implantable signal/pulse generator (IPG) and/or one or more infusion outlets and/or catheters are surgically implanted to infuse drug(s) from an implantable pump. When necessary and/or desired, an SCU provides both electrical stimulation and one or more stimulating drugs. Some forms of the disclosed systems also include one or more sensors for sensing symptoms or other conditions that may indicate a needed treatment.

The SCU used with the present invention possesses one or more of the following properties, among other properties:
- at least two electrodes for applying stimulating current to surrounding tissue and/or a pump and at least one outlet for delivering a drug or drugs to surrounding tissue;
- electronic and/or mechanical components encapsulated in a hermetic package made from biocompatible material(s);
- an electrical coil or other means of receiving energy and/or information inside the package, which receives power and/or data by, for instance, inductive or radio-frequency (RF) coupling to a transmitting coil placed outside the body, thus avoiding the need for electrical leads to connect devices to a central implanted or external controller;
- means for receiving and/or transmitting signals via telemetry;
- means for receiving and/or storing electrical power within the SCU; and
- a form factor making the SCU implantable in a target area in the body.

An SCU may operate independently, or in a coordinated manner with other implanted SCUs, other implanted devices, or with devices external to the patient's body. For instance, an SCU may incorporate means of sensing erectile dysfunction, which information may be used to control the electrical and/or drug simulation parameters in a closed loop manner. The sensing and stimulating means may be incorporated into a single SCU, or a sensing means may communicate sensed information to at least one SCU with stimulating means.

BRIEF DESCRIPTION OF THE SEVERAL VIEWS OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
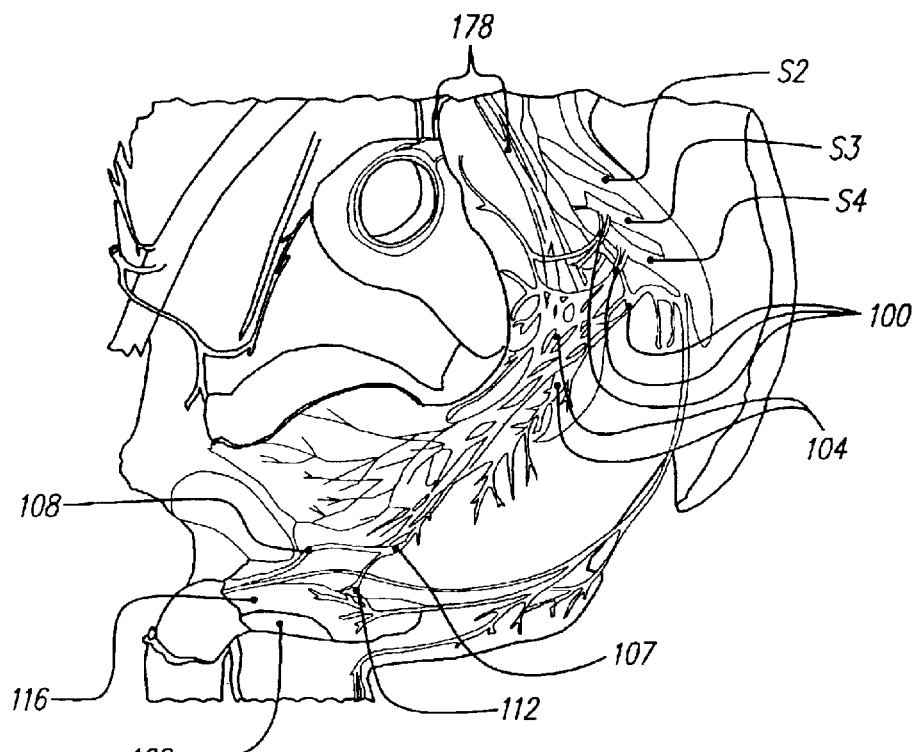
FIG. 1A depicts the nerves of the male pelvic viscera and surrounding anatomy, where a stimulation system of the present invention may be implanted.
Figure 1B:
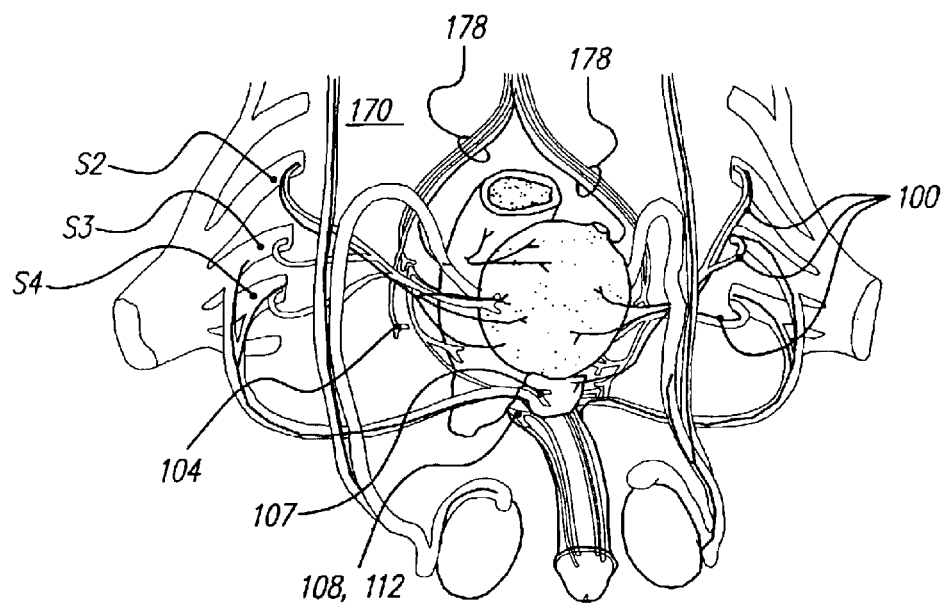
FIG. 1B illustrates the innervation of the male reproductive organs.

FIG. 1A depicts the nerves of a male pelvis, and FIG. 1B is a schematic representation of the sympathetic and parasympathetic fibers of the autonomic nervous system that are responsible for innervation of the male reproductive organs. The parasympathetic input that initiates the male erectile response originates in the pelvic splanchnic nerve plexus. The pelvic splanchnic nerves 100 are comprised of parasympathetic branches from the second, third, and fourth sacral nerves (S2, S3, S4, respectively) that intertwine with the inferior hypogastric plexus 104. Greater cavernous nerve 108 and lesser cavernous nerve 112 are derived from the pelvic splanchnic nerves 100, via the prostatic plexus 107, and carry the parasympathetic input to the corpora cavernosum 116 and corpus spongiosum 128. Sympathetic input from the inferior hypogastric plexus 104 and its branches, which derive from the hypogastric nerves 178 and the sympathetic ganglia, inhibit erection.

Figure 2:
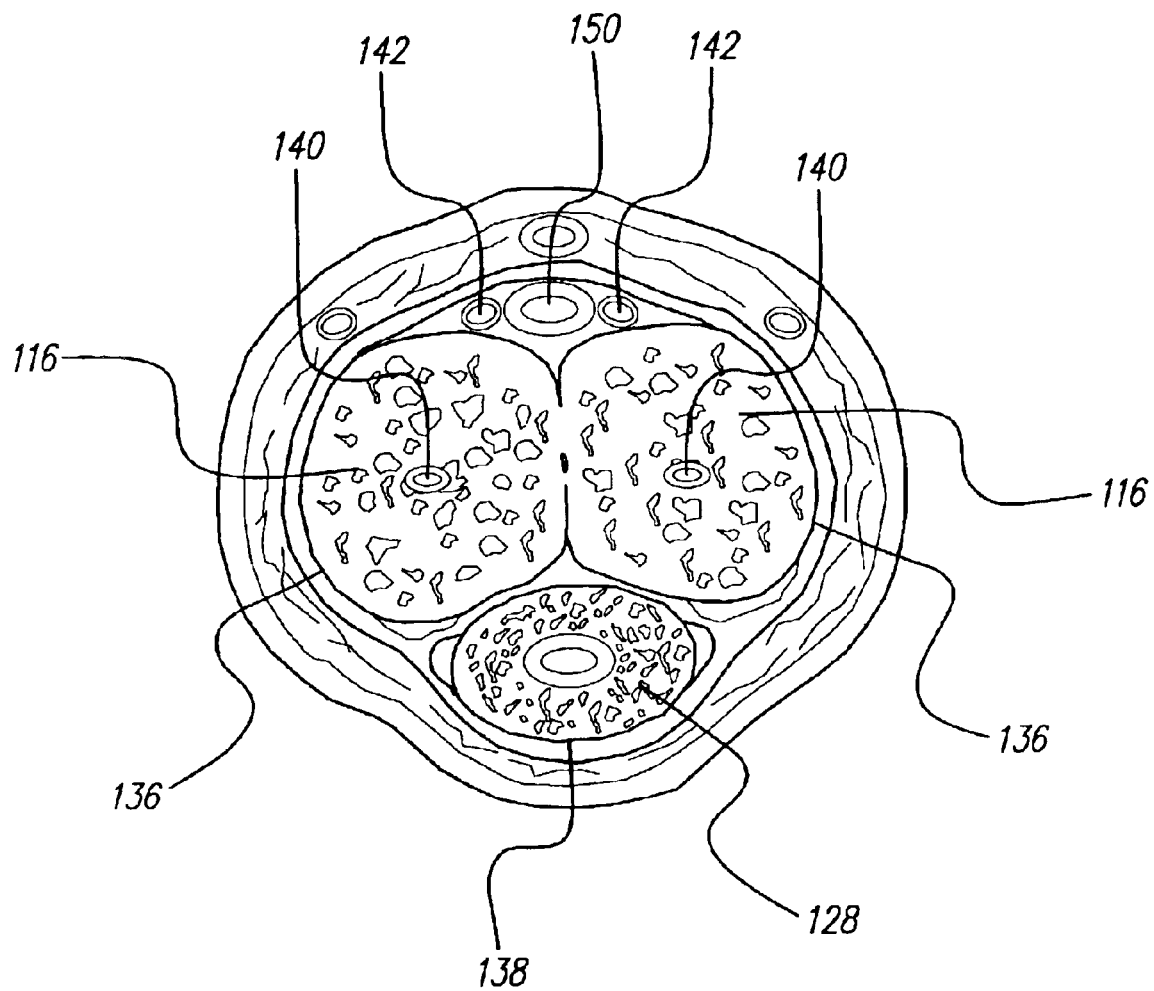
FIG. 2 is a section view through the body of a penis.

Referring next to FIG. 2, the parasympathetic signals carried to the corpora cavernosum 116 and corpus spongiosum 128 cause relaxation of smooth muscle surrounding the arteries and arterioles of the penis and dilation of the arteries and arterioles of the penis. The dilation of the arteries and arterioles causes increased blood flow through the erectile tissue, which leads to expansion of the corpora cavernosa 116 and the corpus spongiosum 128. Due to this expansion, the venous structures draining the penis are compressed against the corpora cavernosum's tunica albuginea 136 and the corpus spongiosum's tunica albuginea 138. Thus, the outflow of blood is restricted, and the internal pressure increases.

Figure 3:
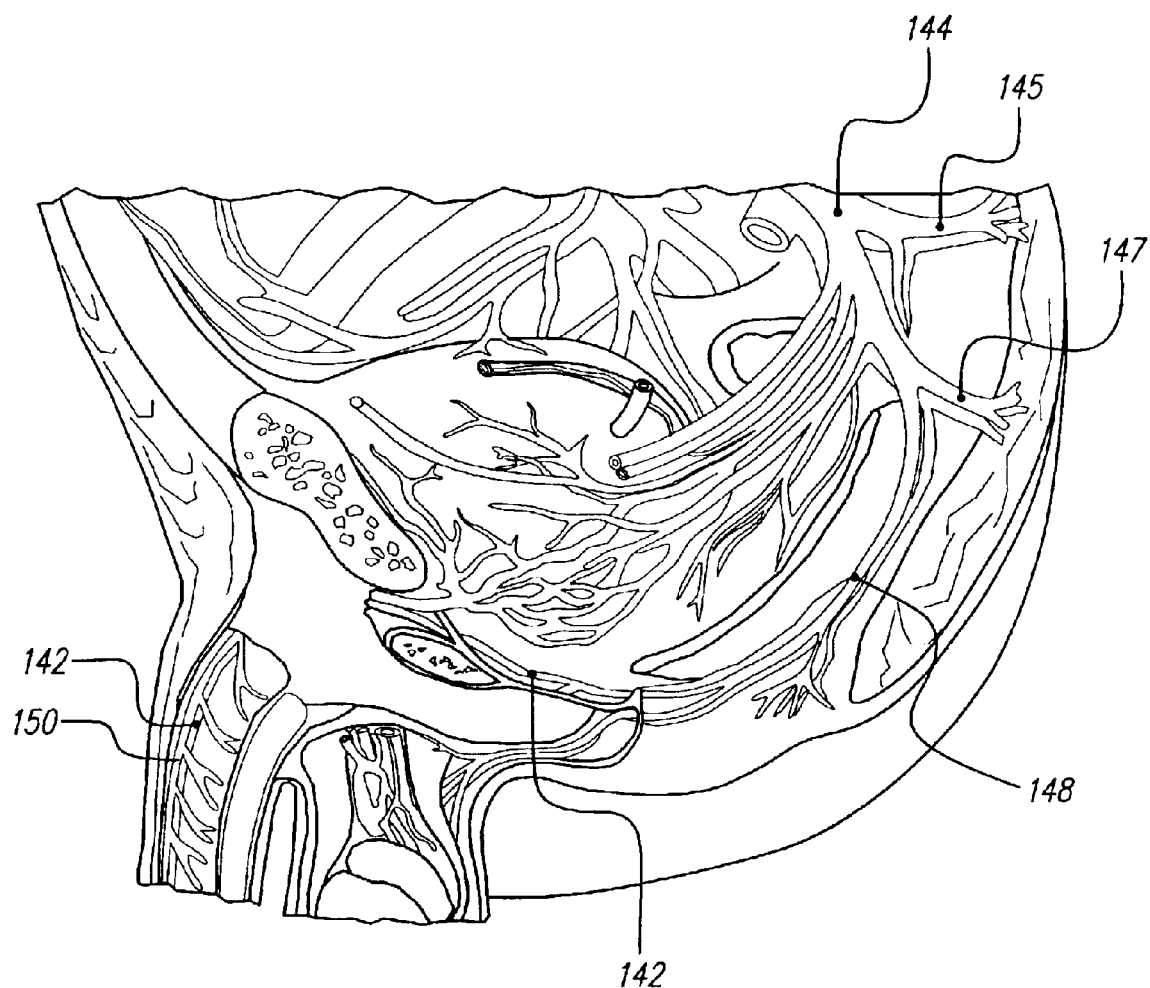
FIG. 3 is left paramedian section view showing the arteries and veins of the male pelvis.

The arteries bringing blood to the cavernous spaces of the penis are the deep arteries of the penis 140 and branches from the dorsal arteries of the penis 142. Referring now to FIG. 3, the internal iliac artery 144, after giving off a superior gluteal artery 145 and an inferior gluteal artery 147, forms the internal pudendal artery 148. The internal pudendal artery 148 branches into the deep arteries of the penis 140 and the dorsal arteries of the penis 142. The dorsal arteries 142 supply blood to the erectile tissue of the glans penis. The deep arteries 140 supply the two corpora cavernosa 116. Some of these arteries assume a tendril-like appearance, forming convoluted and somewhat dilated vessels referred to as helicine arteries. The helicine arteries end in small capillary branches supplying the cavernous spaces, and are most abundant in the back part of the corpora cavernosa 116.

The blood from the cavernous spaces is returned by a series of vessels, some of which emerge in considerable numbers from the base of the glans penis and converge on the dorsum of the organ to form the deep dorsal vein 150; others travel along the upper surface of the corpora cavernosa to join the deep dorsal vein 150; some emerge from the under surface of the corpora cavernosa and wind around the sides of the corpora cavernosa to end in the deep dorsal vein 150; and a number of veins travel separate from the deep dorsal vein 150 and exit at the base of the penis.

The events that promote erection begin with sexual stimulation, which triggers the parasympathetic nervous system to release neurotransmitters. In the penis, the cavernous nerves release neurotransmitters into the endothelial cells of the arteries. Acetylcholine is the neurotransmitter believed to be responsible for triggering the chain of events that leads to a penile erection. Acetylcholine binds to the endothelial cells and causes the synthesis and release of nitric oxide (NO). NO is released from endothelial cells near the corpus cavernosum and diffuses to the smooth muscle cells, where it binds to its target, an enzyme, guanylyl cyclase. Binding of NO to guanylyl cyclase causes a conformational change in the enzyme that leads to an increase in the production of the second messenger guanosine 3',3'-cyclic monophosphate (a.k.a. cyclic GMP or cGMP) from guanosine triphosphate (GTP). The rate of production of cGMP in smooth muscle cells has been observed to increase by at least 400 times due to the interaction of guanylyl cyclase and NO. The increased production of cGMP results in the amplification of the action of cGMP on smooth muscle.

Smooth muscle relaxation in the corpus cavernosum is induced by cGMP, but the way in which it does this is not exactly known. Despite the lack of clarity on the mechanism, it is clear that as long as cGMP remains in the smooth muscle tissue, the muscle is unable to contract. The relaxation of the smooth muscle in the corpus cavernosum allows blood to flow into the penis, where it becomes trapped. The degradation and subsequent disappearance of cGMP from the smooth muscle tissue results in contraction and normal blood flow into and out of the corpus cavernosum. Therefore, cGMP is the final product of several steps needed to initiate, promote, and maintain a penile erection.

The cGMP produced in the smooth muscle tissue of the corpus cavernosum is broken down after a short time. But as long as sexual stimulation continues, the degraded cGMP is continuously replaced by more NO-induced cGMP and erection continues. Cyclic nucleotide phosphodiesterases, specifically Type 5, break down cGMP to GMP by catalyzing a reaction that breaks the phosphodiester bond using $H_2O$. Phosphodiesterase type 5 (PDE5) thereby impedes the actions of cGMP in maintaining penile erection.

Multiple studies in dogs and humans have concluded that sildenafil works by inhibiting PDE5, the enzyme responsible for the degradation of cGMP. Sildenafil, therefore, does not act directly on the corpus cavernosum, but enhances the nitric oxide-cGMP (i.e., NO-cGMP) pathway. More specifically, sildenafil affects the last step in the NO-cGMP pathway. Therefore, all the preceding steps must occur in order to have a penile erection. Sexual stimulation is the trigger to the whole NO-cGMP pathway and this remains true of the pathway when sildenafil is used. Sildenafil helps maintain high levels of cGMP in the corpus cavernosum by preventing PDE5 from breaking it down. Sildenafil's inhibition of PDE5 increases the length of time that cGMP remains in the smooth muscle tissue, and therefore, increases chances of erection. At recommended doses, sildenafil has no effect without sexual stimulation. Vardenafil is anticipated to work in a similar manner and have similar results to sildenafil.

A recent study demonstrated that erectile responses result from treatment of penile tissue with vasodilator agents that elevate cyclic nucleotides in penile cavernosal smooth muscle, including vasoactive intestinal polypeptide (VIP) and $PGE_1$, in addition to sildenafil. The alpha-adrenergic receptor blocking agent phentolamine has been demonstrated to potentiate the effects of vasodilator agents, presumably through its inhibition of sympathetic input to the penis.

As indicated above, the present invention is directed to systems and methods for treating erectile dysfunction, such as erectile dysfunction that follows prostatic surgery. In accordance with the teachings of the present invention, electrical stimulation and/or one or more stimulating drugs are applied to one or more of the above mentioned areas as a treatment for such erectile dysfunction. As used herein, stimulate, stimulation, and stimulating refer to supplying electrical current pulses and/or infusion of a stimulating drug(s). As such, electrical current parameters and/or infusion parameters are sometimes referred to herein as simply stimulation parameters, which parameters may include amplitude, volume, pulse width, infusion rate, and the like. Similarly, stimulation pulses may be pulses of electrical energy and/or pulses of drugs infused by various means and rates of infusion, such as intermittent infusion, infusion at a constant rate, and bolus infusion.

Herein, stimulating drugs comprise medications, anesthetic agents, synthetic or natural hormones, neurotransmitters, interleukins (including cytokines, lymphokines, chemokines, and growth factors), genes, gene products, and other intracellular and intercellular chemical signals and messengers, and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory"drug.

In some alternatives, an implantable signal generator and electrode(s) and/or an implantable pump and catheter(s) are used to deliver electrical stimulation and/or one or more stimulating drugs to the target area(s). One or more electrodes are surgically implanted to provide electrical stimulation, and/or one or more catheters are surgically implanted to infuse the stimulating drug(s).

The invention includes at least one system control unit (SCU). In the case of electrical stimulation only, an SCUs include an implantable pulse/signal generator (IPG), or the like. In the case of drug infusion only, an SCU comprises an implantable pump or the like. In cases requiring both electrical stimulation and drug infusion, more than one SCU may be used. Alternatively, when needed and/or desired, an SCU provides both electrical stimulation and one or more stimulating drugs.

In some embodiments, electrical and/or drug stimulation is provided by one or more system control units (SCUs) that are small, implantable stimulators, referred to herein as microstimulators. The microstimulators of the present invention may be similar to or of the type referred to as BION® devices (see FIGS. 4A, 4B, and 4C). The following documents describe various details associated with the manufacture, operation and use of BION implantable microstimulators, and are all incorporated herein by reference:

| Application/ Patent/ Publication No. | Filing/ Publication Date | Title |
| --- | --- | --- |
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 5,324,316 | Issued Jun. 28, 1994 | Implantable Microstimulator |
| U.S. Pat. No. 5,405,367 | Issued Apr. 11, 1995 | Structure and Method of Manufacture of an Implantable Microstimulator |
| PCT Publication WO 98/37926 | Published Sep. 3, 1998 | Battery-Powered Patient Implantable Device |
| PCT Publication WO 98/43700 | Published Oct. 8, 1998 | System of Implantable Devices For Monitoring and/or Affecting Body Parameters |
| PCT Publication WO 98/43701 | Published Oct. 8, 1998 | System of Implantable Devices For Monitoring and/or Affecting Body Parameters |
| U.S. Pat. No. 6,051,017 (App. No. 09/077,662) | Issued Apr. 18, 2000 (filed May 29, 1998) | Improved Implantable Microstimulator and Systems Employing Same |
|  | Published September 1997 | Micromodular Implants to Provide Electrical Stimulation of Paralyzed Muscles and Limbs, by Cameron, et al., published in IEEE Transactions on Biomedical Engineering, Vol. 44, No. 9, pages 781–790. |

Figure 4A:
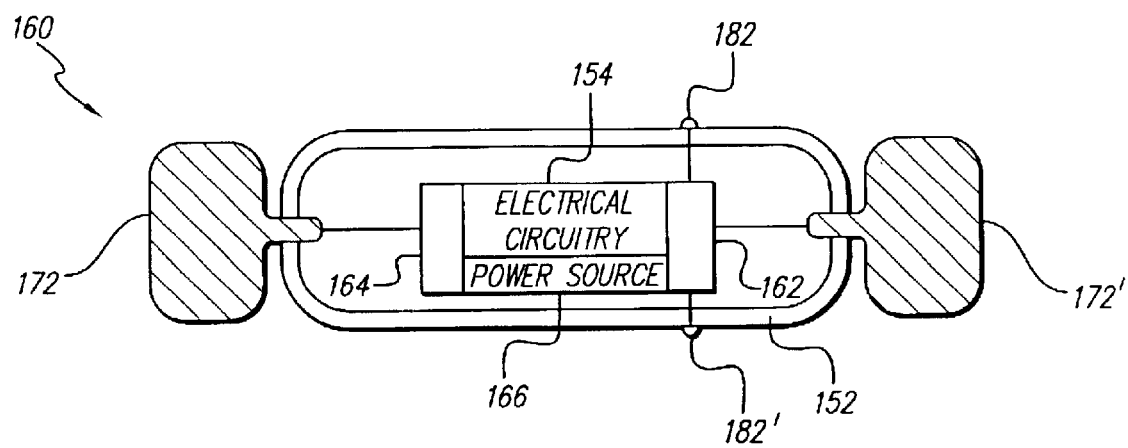
FIGS. 4A, 4B, and 4C show some possible configurations of an implantable microstimulator of the present invention.
Figure 4B:
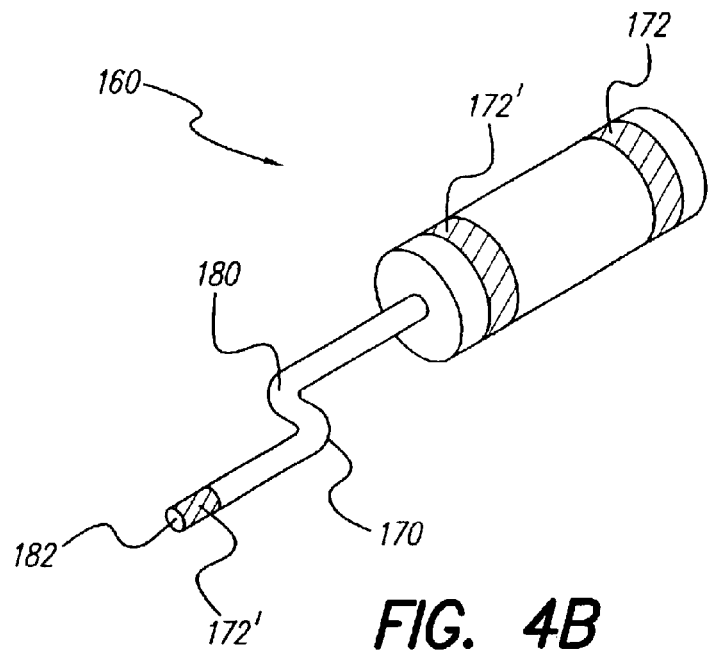
Figure 4C:
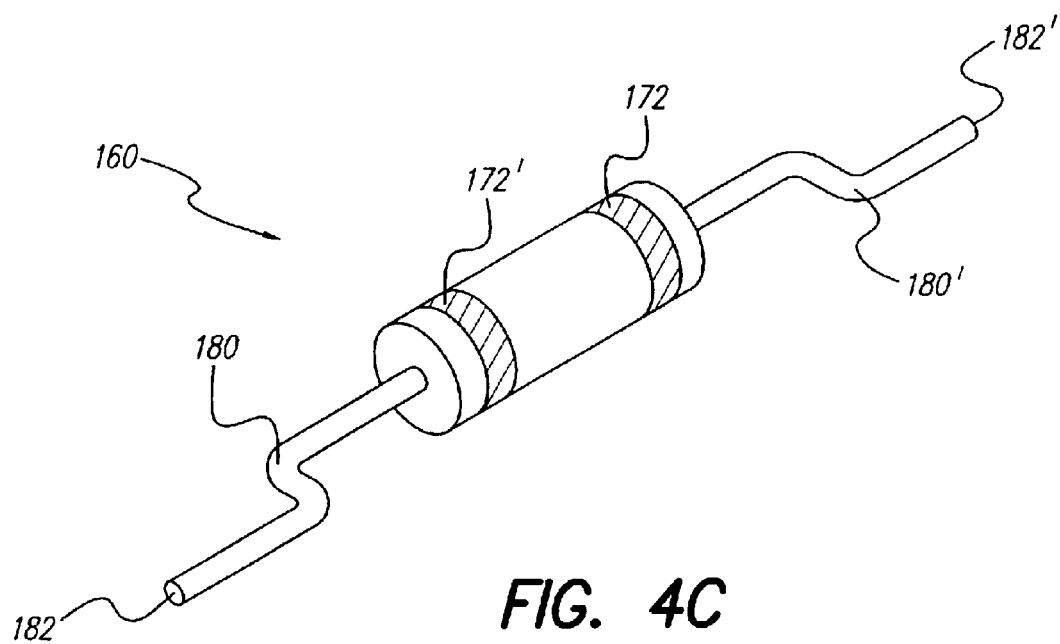

As shown in FIGS. 4A, 4B, and 4C, microstimulator SCUs 160 may include a narrow, elongated capsule 152 containing electronic circuitry 154 connected to electrodes 172 and 172', which may pass through the walls of the capsule at either end. Alternatively, electrodes 172 and/or 172' may be built into the case and/or arranged on a catheter 180 (FIG. 4B) or at the distal portion of a lead, as described below. As detailed in the referenced patents, electrodes 172 and 172' generally comprise a stimulating electrode (to be placed close to the target tissue) and an indifferent electrode (for completing the circuit). Other configurations of microstimulator SCU 160 are possible, as is evident from the above-referenced patent publications, and as described in more detail herein.

Certain configurations of SCU 160 are sufficiently small to permit placement in or adjacent to the structures to be stimulated. For instance, in these configurations, capsule 152 may have a diameter of about 4–5 mm, or only about 3 mm, or even less than about 3 mm. In these configurations, capsule length may be about 25–35 mm, or only about 20–25 mm, or even less than about 20 mm. The shape of the microstimulator may be determined by the structure of the desired target, the surrounding area, and the method of implantation. A thin, elongated cylinder with electrodes at the ends, as shown in FIGS. 4A, 4B, and 4C, is one possible configuration, but other shapes, such as cylinders, disks, spheres, and helical structures, are possible, as are different configurations of and/or additional electrodes, infusion outlets, leads, and/or catheters.

Microstimulator SCU 160, when certain configurations are used, may be implanted with a surgical tool such as a tool specifically designed for the purpose, or may be placed, for instance, via a small incision and through an insertion cannula. Alternatively, microstimulator SCU 160 may be implanted via conventional surgical methods, or may be implanted using other endoscopic or laparoscopic techniques. A more complicated surgical procedure may be required for sufficient access to a portion of a nerve and/or for fixing the microstimulator in place.

The external surfaces of microstimulator SCU 160 may advantageously be composed of biocompatible materials. Capsule 152 may be made of, for instance, glass, ceramic or other material that provides a hermetic package that will exclude water vapor but permit passage of electromagnetic fields used to transmit data and/or power. Electrodes 172 and 172' may be made of a noble or refractory metal or compound, such as platinum, iridium, tantalum, titanium, titanium nitride, niobium, or alloys or any of these, in order to avoid corrosion or electrolysis which could damage the surrounding tissues and the device.

In certain embodiments of the instant invention, microstimulator SCU 160 comprises two, leadless electrodes. However, either or both electrodes 172 and 172' may alternatively be located at the distal portion of short, flexible leads as described in U.S. patent application Ser. No. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of microstimulator SCU 160, while allowing most elements of the microstimulator to be located in a more surgically convenient site. This minimizes the distance traversed and the surgical planes crossed by the device and any lead(s). In most uses of this invention, the leads are no longer than about 150 mm.

Figure 5:
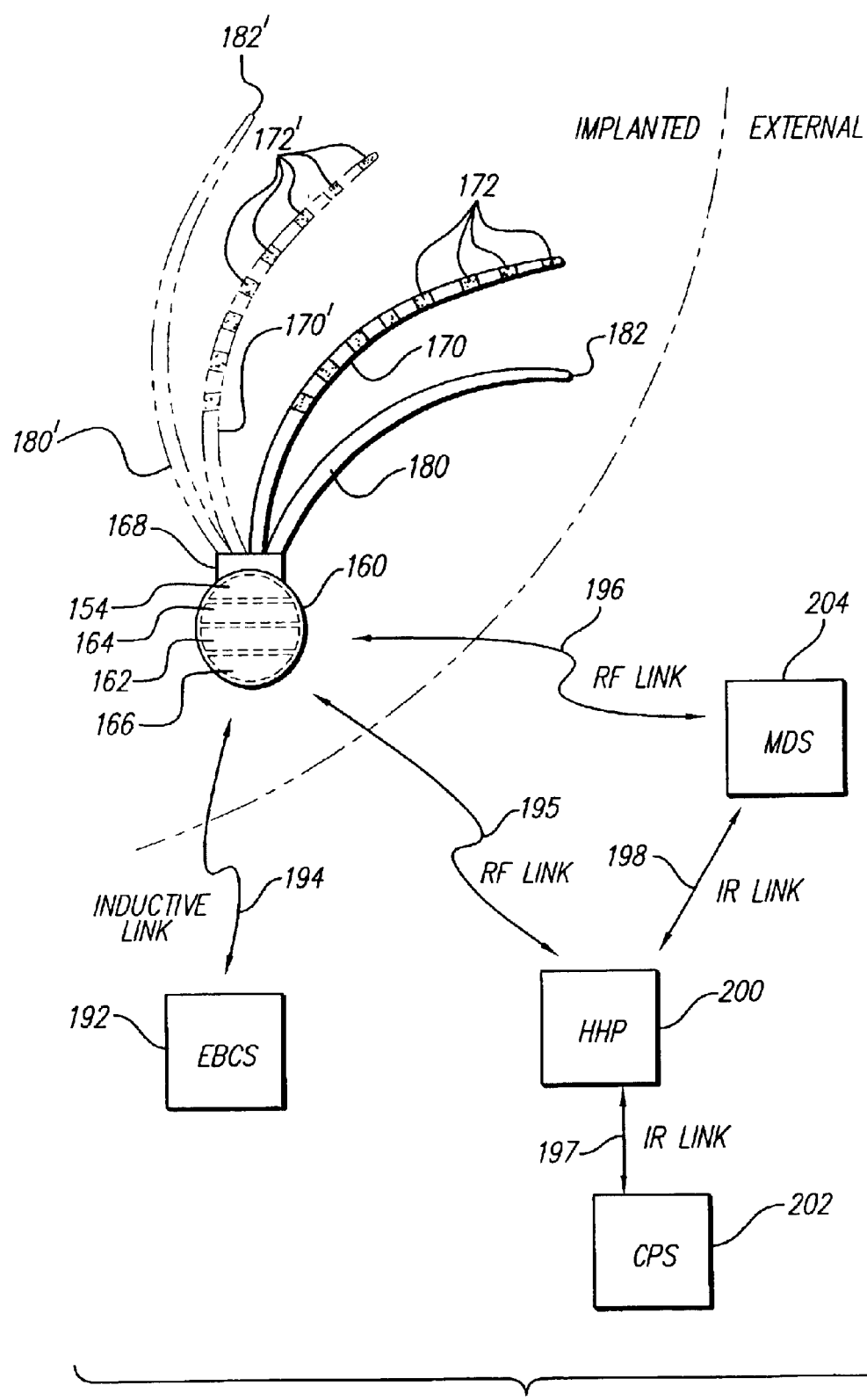
FIG. 5 depicts internal and external components of certain embodiments of the invention.

As seen in FIG. 5, some embodiments of SCU 160 may be (but are not necessarily) implanted in a surgically-created shallow depression or opening, such as in the abdomen, pelvis, thorax, or above the buttock. In such embodiments, SCU 160 may conform to the profile of surrounding tissue(s) and/or bone(s), and is small and compact. This may minimize upward pressure applied to the skin, which pressure may cause skin erosion or infection. Thus, in some embodiments, SCU 160 has a diameter of about 75 mm, or only about 65 mm, or even less than about 55 mm. In these configurations, SCU thickness may be approximately 10–12 mm, or even less than about 10 mm.

As depicted in FIG. 5, in some embodiments, one or more electrode leads 170 and/or catheters 180 attached to SCU 160 run subcutaneously, for instance, in a surgically-created shallow groove(s) or channel(s) or in a fascial plane(s) to the tissue to be stimulated. Recessed placement of the SCU and the lead(s) and/or catheter(s) may decrease the likelihood of erosion of overlying skin, and may minimize any cosmetic impact.

In embodiments such as in FIG. 5, electrode(s) 172 are carried on lead 170 having a proximal portion coupled to SCU 160. The lead contains wires electrically connecting electrodes 172 to SCU 160. SCU 160 contains electrical components 154 that produce electrical stimulation pulses that travel through the wires of lead 170 and are delivered to electrodes 172, and thus to the tissue surrounding electrodes 172. To protect the electrical components inside SCU 160, some or all of the case of the SCU may be hermetically sealed. For additional protection against, e.g., impact, the case may be made of metal (e.g. titanium) or ceramic, which materials are also biocompatible. In addition, SCU 160 may be configured to be Magnetic Resonance Imaging (MRI) compatible.

In the case of treatment alternatively or additionally constituting drug infusion, SCU 160 may contain at least one pump 162 for storing and dispensing one or more drugs through infusion outlet(s) 182 and/or catheter(s) 180 into a predetermined site. When a catheter is used, it includes at least one infusion outlet 182, usually positioned at least at a distal end, and/or positioned at a distal portion of the catheter, while a proximal portion of the catheter is connected to SCU 160.

According to some embodiments of the invention, such as depicted in FIG. 5, at least one lead 170 is attached to SCU 160, via a suitable connector 168, if necessary. Each lead includes at least two electrodes 172, and may include as many as sixteen or more electrodes 172, positioned at a distal portion of the lead (as used herein, "at a distal portion" includes at the tip or anywhere on the distal end or section of the lead). Additional leads 170' and/or catheter(s) 180' may be attached to SCU 160. Hence, FIG. 5 shows (in phantom lines) a second catheter 180', and a second lead 170', having electrodes 172' thereon, also attached to SCU 160. Similarly, the SCUs 160 of FIGS. 4A, 4B, and 4C have outlets 182, 182' for infusing a stimulating drug(s) and electrodes 172, 172' for applying electrical stimulation.

Lead(s) 170/170' of certain embodiments of the present invention may be less than about 5 mm in diameter, or even less than about 1.5 mm in diameter. Electrodes 172/172' on leads 170/170' may be arranged as an array, for instance, as two or more collinear electrodes, or even as four or more collinear electrodes, or they may not be collinear. A tip electrode may also be supplied at the distal end of one or more leads. In some embodiments, SCU 160 is programmable to produce either monopolar electrical stimulation, e.g., using the SCU case as an indifferent electrode, or bipolar electrical stimulation, e.g., using one of the electrodes of the electrode array as an indifferent electrode. Some embodiments of SCU 160 have at least four channels and drive up to sixteen electrodes or more.

SCU 160 (which herein refers to IPGs, implantable pumps, IPG/pump combinations, microstimulators for drug and/or electrical stimulation, other alternative devices described herein, and the like) contains, when necessary and/or desired, electronic circuitry 154 for receiving data and/or power from outside the body by inductive, radio frequency (RF), or other electromagnetic coupling. In some embodiments, electronic circuitry 154 includes an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), and the like.

SCU 160 also includes, when necessary and/or desired, a programmable memory 164 for storing a set(s) of data, stimulation, and control parameters. Among other things, memory 164 may allow electrical and/or drug stimulation to be adjusted to settings that are safe and efficacious with minimal discomfort for each individual. Specific parameters may provide therapy for various types and degrees of erectile dysfunction. For instance, some patients may respond favorably to intermittent stimulation, while others may require continuous treatment to treat their dysfunction. In some embodiments, electrical and drug stimulation parameters are controlled independently. In various embodiments, they are coupled, e.g., electrical stimulation is programmed to occur only during drug infusion.

In addition, parameters may be chosen to target specific tissues and to exclude others. For example, parameters may be chosen to increase neural activity in specific neural populations and to decrease neural activity in others. As another example, relatively low frequency neurostimulation (i.e., less than about 50–100 Hz) typically has an excitatory effect on surrounding neural tissue, leading to increased neural activity, whereas relatively high frequency neurostimulation (i.e., greater than about 50–100 Hz) may have an inhibitory effect, leading to decreased neural activity.

Similarly, excitatory neurotransmitters (e.g., acetylcholine), agonists thereof, and agents that increase levels of an excitatory neurotransmitter(s) (e.g., edrophonium) generally have an excitatory effect on neural tissue, while inhibitory neurotransmitters (e.g., gamma-aminobutyric acid, a.k.a. GABA), agonists thereof, and agents that act to increase levels of an inhibitory neurotransmitter(s) generally have an inhibitory effect. However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g., atropine, oxybutynin) and agents that decrease levels of excitatory neurotransmitters may inhibit neural activity.

Some embodiments of SCU 160 also include a power source and/or power storage device 166. Possible power options for a stimulation device of the present invention, described in more detail below, include but are not limited to an external power source coupled to the stimulation device, e.g., via an RF link, a self-contained power source utilizing any means of generation or storage of energy (e.g., a primary battery, a replenishable or rechargeable battery such as a lithium ion battery, an electrolytic capacitor, or a super- or ultra-capacitor), and if the self-contained power source is replenishable or rechargeable, means of replenishing or recharging the power source (e.g., an RF link, an optical link, a thermal link, or other energy-coupling link).

In embodiments such as shown in FIG. 5, SCU 160 includes a rechargeable battery as a power source/storage device 166. The battery is recharged, as required, from an external battery charging system (EBCS) 192, typically through an inductive link 194. In these embodiments, SCU 160 includes a processor and other electronic circuitry 154 that allow it to generate stimulation pulses that are applied to a patient 208 through electrodes 172 and/or outlet(s) 182 in accordance with a program and stimulation parameters stored in programmable memory 164. Stimulation pulses of drugs include various types and/or rates of infusion, such as intermittent infusion, infusion at a constant rate, and bolus infusion.

According to certain embodiments of the invention, an SCU operates independently. According to various embodiments of the invention, an SCU operates in a coordinated manner with other SCU(s), other implanted device(s), or other device(s) external to the patient's body. For instance, an SCU may control or operate under the control of another implanted SCU(s), other implanted device(s), or other device(s) external to the patient's body. An SCU may communicate with other implanted SCUs, other implanted devices, and/or devices external to a patient's body via, e.g., an RF link, an ultrasonic link, a thermal link, or an optical link. Specifically, an SCU may communicate with an external remote control (e.g., patient and/or physician programmer) that is capable of sending commands and/or data to an SCU and that may also be capable of receiving commands and/or data from an SCU.

For example, some embodiments of SCU 160 of the present invention may be activated and deactivated, programmed and tested through a hand held programmer (HHP) 200 (which may also be referred to as a patient programmer and may be, but is not necessarily, hand held), a clinician programming system (CPS) 202 (which may also be hand held), and/or a manufacturing and diagnostic system (MDS) 204 (which may also be hand held). HHP 200 may be coupled to SCU 160 via an RF link 195. Similarly, MDS 204 may be coupled to SCU 160 via another RF link 196. In a like manner, CPS 202 may be coupled to HHP 200 via an infra-red link 197; and MDS 204 may be coupled to HHP 200 via another infra-red link 198. Other types of telecommunicative links, other than RF or infra-red may also be used for this purpose. Through these links, CPS 202, for example, may be coupled through HHP 200 to SCU 160 for programming or diagnostic purposes. MDS 204 may also be coupled to SCU 160, either directly through the RF link 196, or indirectly through IR link 198, HHP 200, and RF link 195.

Figure 6:
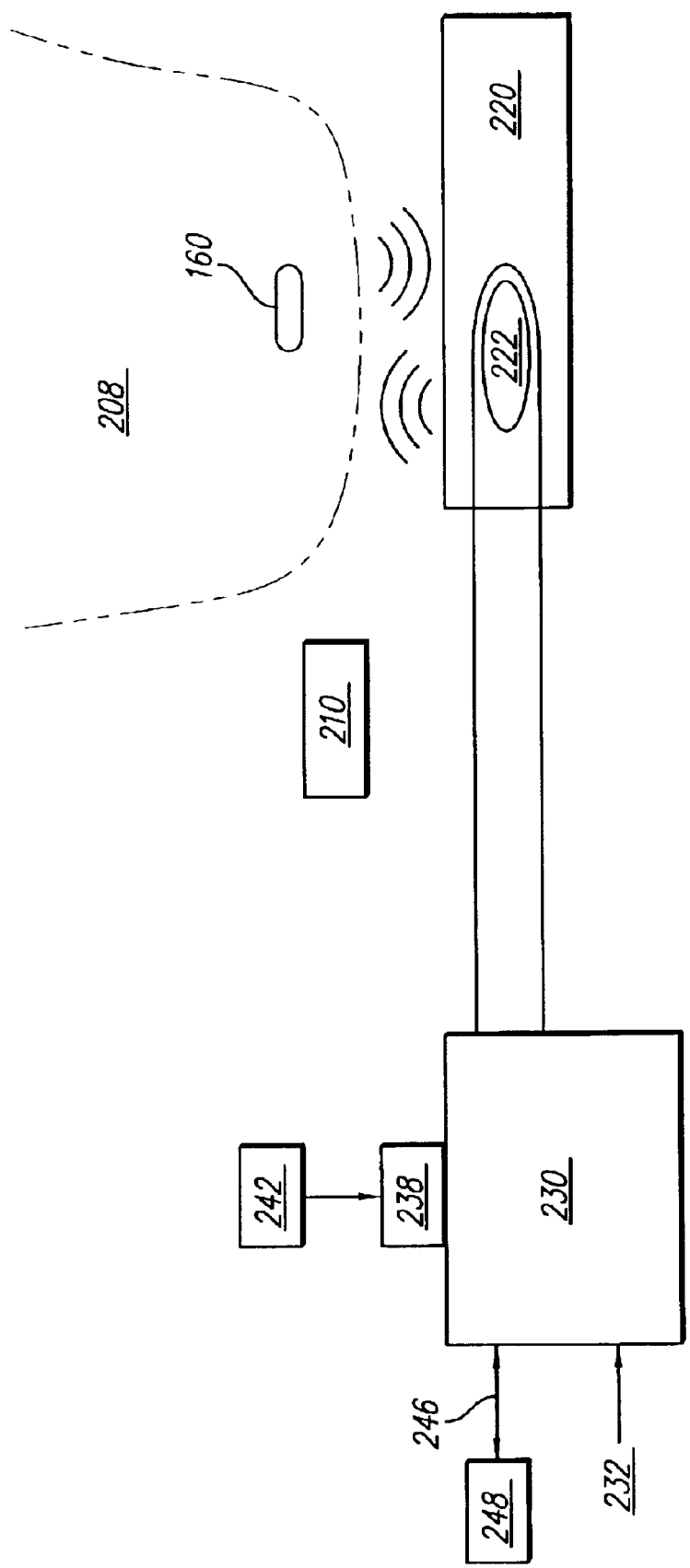
FIG. 6 illustrates internal and external components of various embodiments of the invention.

In certain embodiments, using for example, a microstimulator(s) as described herein, and as illustrated in FIG. 6, the patient 208 switches SCU 160 on and off by use of controller 210, which may be handheld. Controller 210 operates to control SCU 160 by any of various means, including sensing the proximity of a permanent magnet located in controller 210, sensing RF transmissions from controller 210, or the like. Other means of controlling SCU are possible, such as an implanted button that may be pressed to activate SCU 160.

External components of various embodiments for programming and providing power to SCU 160 are also illustrated in FIG. 6. When it is required to communicate with SCU 160, patient 208 is positioned on or near external appliance 220, which appliance contains one or more inductive coils 222 or other means of communication (e.g., RF transmitter and receiver). External appliance 220 is connected to or is a part of external electronic circuitry appliance 230 which may receive power 232 from a conventional power source. External appliance 230 contains manual input means 238, e.g., a keypad, whereby the patient 208 or a caregiver 242 may request changes in electrical and/or drug stimulation parameters produced during the normal operation of SCU 160. In these embodiments, manual input means 238 include various electromechanical switches and/or visual display devices that provide the patient and/or caregiver with information about the status and prior programming of SCU 160.

Alternatively or additionally, external electronic appliance 230 is provided with an electronic interface means 246 for interacting with other computing means 248, such as by a serial interface cable or infrared link to a personal computer, to a telephone modem, or the like. Such interface means 246 may permit a clinician to monitor the status of the implant and prescribe new stimulation parameters from a remote location.

The external appliance(s) may be embedded in a cushion, pillow, mattress cover, or garment. Other possibilities exist, including a belt, patch, or other structure(s) that may be affixed to the patient's body or clothing. External appliances may include a package that can be, e.g., worn on the belt, may include an extension to a transmission coil affixed to the body, e.g., with a velcro band or adhesive, or may be combinations of these or other structures able to perform the functions described herein.

To help determine the strength and/or duration of electrical stimulation and/or the amount and/or type(s) of stimulating drug(s) required to produce the desired effect, in some embodiments, a patient's response to and/or need for treatment is sensed. For example, changes in penile arteriole pressure produced in response to stimulation may be sensed. Other measures of the state of the patient may additionally or alternatively be sensed, e.g., pressure in corpus cavemosum, pressure in corpus spongiosum, joint angle, tumescence, muscle activity (e.g., EMG), nerve activity (e.g., ENG, cavernous nerve firing rate), electrical activity of the brain (e.g., EEG), neurotransmitter levels and/or their associated breakdown product levels, hormone levels, interleukin levels, or other substances, such as ketone, electrolyte, enzyme, and/or medication levels, and/or changes in these or other substances in the blood plasma or local interstitial fluid, may be sensed. Substances may be sensed, for instance, using one or more Chemically Sensitive Field-Effect Transistors (CHEMFETs) such as Enzyme-Selective Field-Effect Transistors (ENFETs) or Ion-Sensitive Field-Effect Transistors (ISFETs, as are available from Sentron CMT of Enschede, The Netherlands).

For example, when electrodes and/or catheters of SCU 160 are implanted adjacent to greater cavernous nerve 108, signals from a pressure sensor built into SCU 160 may be recorded. (As used herein, "adjacent" and "near" mean as close as reasonably possible to targeted tissue, including touching, being attached to, or even being positioned within the tissue, but in general, may be as far as about 150 mm from the target tissue. In addition, as used herein, "tissue affecting the penis" includes tissue of the penis itself.)

Alternatively, an "SCU" dedicated to sensory processes communicates with an SCU that provides the stimulation pulses. The implant circuitry 154 may, if necessary, amplify and transmit these sensed signals, which may be digital or analog. Other methods of determining the required electrical and/or drug stimulation include observing the stimulation required to initiate and maintain erection, as well as other methods mentioned herein, and others that will be evident to those of skill in the art upon review of the present disclosure. The sensed information may be used to control stimulation parameters in a closed-loop manner.

For instance, in several embodiments of the present invention, a first and second "SCU" are provided. The second "SCU" periodically (e.g., once per minute) records a level of muscle activity (or neural activity, etc.), which it transmits to the first SCU. The first SCU uses the sensed information to adjust electrical and/or drug stimulation parameters according to an algorithm programmed, e.g., by a physician. For example, the amplitude of electrical stimulation may be increased in response to decreased penile arteriole pressure. In some alternatives, one SCU performs both the sensing and stimulating functions, as discussed in more detail presently.

While an SCU 160 may also incorporate means of sensing dysfunction, it may alternatively or additionally be desirable to use a separate or specialized implantable device to record and telemeter physiological conditions/responses in order to adjust electrical stimulation and/or drug infusion parameters. This information may be transmitted to an external device, such as external appliance 220, or may be transmitted directly to implanted SCU(s) 160. However, in some cases, it may not be necessary or desired to include a sensing function or device, in which case stimulation parameters are determined and refined, for instance, by patient feedback, or the like.

Thus, it is seen that in accordance with the present invention, one or more external appliances may be provided to interact with SCU 160, and may be used to accomplish, potentially among other things, one or more of the following functions:

Function 1: If necessary, transmit electrical power from the external electronic appliance 230 via appliance 220 to SCU 160 in order to power the device and/or recharge the power source/storage device 166. External electronic appliance 230 may include an automatic algorithm that adjusts electrical and/or drug stimulation parameters automatically whenever the SCU(s) 160 is/are recharged.

Function 2: Transmit data from the external appliance 230 via the external appliance 220 to SCU 160 in order to change the parameters of electrical and/or drug stimulation produced by SCU 160.

Function 3: Transmit sensed data indicating a need for treatment or in response to stimulation from SCU 160 (e.g., impedance, pressure, joint angle, electromyographical activity, level of a blood-borne substance(s), or other activity) to external appliance 230 via external appliance 220.

Function 4: Transmit data indicating state of the SCU 160 (e.g., battery level, drug level, stimulation parameters, etc.) to external appliance 230 via external appliance 220.

By way of example, a treatment modality for erectile dysfunction may be carried out according to the following sequence of procedures:

1. An SCU 160 is implanted so that at least one infusion outlet 182 is adjacent to greater cavernous nerve 108 and/or a blood vessel(s) supplying the penis (e.g., left and/or right deep artery of the penis). If necessary or desired, electrodes 172, 172' and/or additional infusion outlet(s) 182' may be implanted adjacent cavernous nerve 108 and/or other nerve fibers, blood vessels, or other tissue, such as the lesser cavernous nerve 112, corpus cavernosum 116, and/or corpus spongiosum 128.

2. Using Function 2 described above (i.e., transmitting data) of external electronic appliance 230 and external appliance 220, SCU 160 is commanded to infuse a parasympathetic agonist, e.g., acetylcholine, and/or nitric oxide or an agonist thereof, possibly in gradually increasing amounts, and possibly while producing a series of excitatory electrical stimulation pulses, possibly with gradually increasing amplitude. Alternatively, SCU 160 may be commanded to produce a series of excitatory electrical stimulation pulses, possibly with gradually increasing amplitude, and possible while infusing a parasympathetic agonist and/ or nitric oxide or an agonist thereof, possibly in gradually increasing amounts.

3. After each stimulating infusion pulse, series of pulses, or at some other predefined interval, any change in arteriole pressure in arteries supplying the penis (and/or intra-cavernosal pressure) resulting from the stimulation is sensed, for instance, by one or more electrodes 172 and/or 172' or sensors. These responses are converted to data and telemetered out to external electronic appliance 230 via Function 3.

4. From the response data received at external appliance 230 from SCU 160, the stimulus threshold for obtaining a response is determined and is used by a clinician 242 acting directly 238 or by other computing means 248 to transmit the desired drug and/or electrical stimulation parameters to SCU 160 in accordance with Function 2.

5. When patient 208 desires to invoke electrical stimulation and/or drug infusion to instigate erection, he employs controller 210 to set SCU 160 in a state where it delivers a prescribed stimulation pattern from a predetermined range of allowable stimulation patterns.

6. To allow his penis to return to a flaccid state, patient 208 employs controller 210 to turn off SCU 160.

7. Periodically, the patient or caregiver recharges the power source/storage device 166 of SCU 160, if necessary, in accordance with Function 1 described above (i.e., transmit electrical power).

For the treatment of any of the various types and degrees of erectile dysfunction, it may be desirable to modify or adjust the algorithmic functions performed by the implanted and/or external components, as well as the surgical approaches, in ways that would be obvious to skilled practitioners of these arts. For example, in some situations, it may be desirable to employ more than one SCU 160, each of which could be separately controlled by means of a digital address. Multiple channels and/or multiple patterns of electrical and/or drug stimulation might thereby be programmed by the clinician and controlled by the patient in order to deal with complex dysfunctions such as severe erectile dysfunction that requires stimulation of multiple nerves, e.g., bilateral greater and lesser cavernous nerves, or for multiple dysfunctions e.g., erectile dysfunction and incontinence.

In some embodiments discussed earlier, SCU 160, or a group of two or more SCUs, is controlled via closed-loop operation. A need for and/or response to stimulation is sensed via SCU 160, or by an additional SCU (which may or may not be dedicated to the sensing function), or by another implanted or external device. If necessary, the sensed information is transmitted to SCU 160. In some embodiments, the stimulation parameters used by SCU 160 are automatically adjusted based on the sensed information. Thus, the electrical and/or drug stimulation parameters may be adjusted in a closed-loop manner to provide stimulation tailored to the need for and/or response to the electrical and/or drug stimulation.

Figure 7:
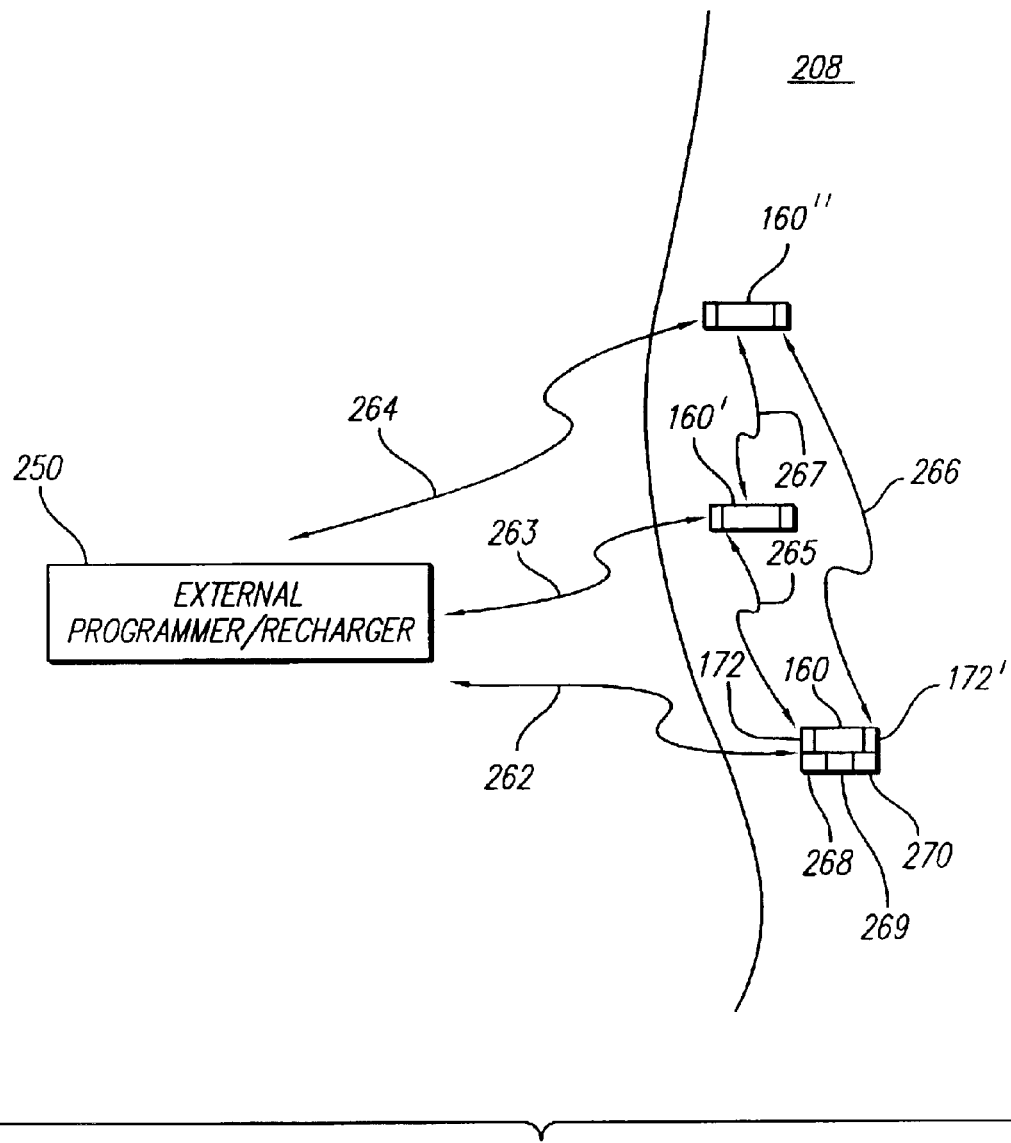
FIG. 7 depicts a system of implantable devices that communicate with each other and/or with external control/programming devices.

For instance, as shown in the example of FIG. 7, a first SCU 160, implanted beneath the skin of the patient 208, provides a first medication or substance; a second SCU 160' provides a second medication or substance; and a third SCU 160" provides electrical stimulation via electrodes 172 and 172'. As mentioned earlier, the implanted devices may operate independently or may operate in a coordinated manner with other similar implanted devices, other implanted devices, or other devices external to the patient's body, as shown by the control lines 262, 263 and 264 in FIG. 7. That is, in accordance with certain embodiments of the invention, the external controller 250 controls the operation of each of the implanted devices 160, 160' and 160". According to various embodiments of the invention, an implanted device, e.g. SCU 160, may control or operate under the control of another implanted device(s), e.g. SCU 160' and/or SCU 160". That is, a device made in accordance with the invention may communicate with other implanted stimulators, other implanted devices, and/or devices external to a patient's body, e.g., via an RF link, an ultrasonic link, an optical link, or the like. Specifically, as illustrated in FIG. 7, SCU 160, 160', and/or 160", made in accordance with the invention, may communicate with an external remote control (e.g., patient and/or physician programmer 250) that is capable of sending commands and/or data to implanted devices and that may also be capable of receiving commands and/or data from implanted devices.

A drug infusion stimulator made in accordance with the invention may incorporate communication means for communicating with one or more external or site-specific drug delivery devices, and, further, may have the control flexibility to synchronize and control the duration of drug delivery. The associated drug delivery device typically provides a feedback signal that lets the control device know it has received and understood commands. The communication signal between the implanted stimulator and the drug delivery device may be encoded to prevent the accidental or inadvertent delivery of drugs by other signals.

An SCU made in accordance with some embodiments of the invention thus incorporates first sensing means 268 for sensing therapeutic effects, clinical variables, or other indicators of the state of the patient, such as ENG, EMG, EEG, pressure, joint angle, tumescence, impedance, or the like. The stimulator additionally or alternatively incorporates second means 269 (e.g., a CHEMFET) for sensing neurotransmitter levels and/or their associated breakdown product levels, medication levels and/or other drug levels, hormone, ketone, electrolytes, enzyme, and/or interleukin levels and/or changes in these or other substances in the blood plasma or local interstitial fluid. The stimulator additionally or alternatively incorporates third means 270 for sensing electrical current levels and/or waveforms supplied by another source of electrical energy. Sensed information may be used to control infusion and/or electrical parameters in a closed loop manner, as shown by control lines 266, 267, and 265. Thus, sensing means may be incorporated into a device that also includes electrical and/or drug stimulation, or the sensing means (that may or may not have stimulating means) may communicate the sensed information to another device(s) with stimulating means.

As indicated above, during nerve-sparing prostate surgery, the cavernous nerves are typically visualized and may be stimulated acutely for improved localization and identification. During the procedure, if the cavernous nerves are identified, then according to certain embodiments of the present invention, a means of stimulation, such as electrodes 172/172' are placed adjacent to one or more cavernous nerves and/or adjacent (such as within) other tissue(s) or blood vessel(s). In various embodiments, when such nerves are identified, infusion outlet(s) 182/182' of catheter(s) 180/180' are placed adjacent to one or both cavernous nerves 108/112 or adjacent the corpus cavernosum 116 and/or other tissue(s) or blood vessel(s) to infuse stimulating dosages of one or more drugs. The lead(s) 170/170' and/or catheter(s) 180/180' exit the patient through the surgical entry site or another site created for exit, thus providing stimulation of the cavernous nerve(s) 108/112 and/or other site(s).

Following surgery, the patient may regain normal erectile function. Therefore, the lead(s)/catheter(s) may be designed for easy removal with minimal or no surgical intervention. For instance, in-line lead(s) may be used, which may simply be pulled out, or the lead(s)/catheter(s) may have a barb(s), which can be broken or overcome with minimal force. Alternatively, the proximal portion of the lead(s)/catheter(s) may be placed in a subcutaneous pocket under the skin and left in place, or the proximal portion may be severed and the exit site closed over the remaining portion of the lead.

If the patient does not regain normal erectile function following surgery, then according to the teachings of the present invention, the patient undergoes testing to determine if stimulation produces erection. Such testing may include connecting the proximal portion of the lead(s)/catheter(s) to an external stimulator which provides stimulation pulses through the electrode(s) and/or infusion outlet(s) in order to assess patient response to such stimulation. If erection is achieved with stimulation, then the patient may elect to have the proximal portion of the lead(s)/catheter(s) attached to SCU 160, which is then implanted in the patient. In such cases, treatment is carried out as described earlier, with lead(s) 170/170' and/or catheter(s) 180/180' coupled at a proximal portion to SCU 160 and having electrode portion(s) 172/172' and/or catheter infusion outlet(s) 182/182' providing stimulation to one or more of the cavernous nerves 108/112, corpus cavernosum 116, and/or other tissue(s) or blood vessel(s).

As a therapeutic alternative, electrode portion(s) 172/172' and/or infusion outlet(s) 182/182' may additionally or alternatively be implanted adjacent any structure or space of the penis, such as corpus cavernosa 116, corpus spongiosum 128, and/or parasympathetic targets deeper in the patients body, such as one or more of the proximal portion of cavernous nerves 108 and 112, the prostatic plexus 107, the pelvic splanchnic nerves 100, and the second, third, and fourth sacral nerves $S_2$, $S_3$, $S_4$. Electrodes 172/172' and/or infusion outlet(s) 182/182' may also or instead be implanted adjacent to one or more of the hypogastric nerves 178, certain nerves of the inferior hypogastric plexus 104 or its branches, or the sympathetic ganglia from which they arise, in order to inhibit sympathetic input that retards erection. Infusion outlet(s) 182/182' and/or electrodes 172/172' may also or instead be implanted adjacent (e.g., within) any blood vessel supplying or draining the penis, including the left and right internal iliac arteries 144, the left and right internal pudendal arteries 148, the left and right dorsal arteries of the penis 142, the left and right deep arteries of the penis 140, the deep dorsal vein 150 of the penis, and the urethra.

As yet another therapeutic alternative, one or more microstimulator SCUs such as described earlier may be implanted to apply electrical and/or drug stimulation to any of the above named structures. The microstimulator SCU(s) may be implanted at any time, such as during prostate surgery. If not needed or desired after surgery, the microstimulator(s) may remain implanted, or may be explanted. Alternatively, microstimulator SCUs may be implanted after prostate surgery, or at any other time, to address erectile dysfunction.

According to certain embodiments, the patient is treated with increased excitement of the parasympathetic input to the penis. Relatively low-frequency electrical stimulation (e.g., less than about 50–100 Hz) is likely to produce such excitement. Additionally or alternatively, substances that may be infused to promote erection include neurotransmitters and medications that act to increase parasympathetic activation, such as acetylcholine and its agonists (i.e., cholinergic medications), androgens (e.g., testosterone), alpha-adrenergic antagonists (e.g., phentolamine), prostaglandins (e.g., prostaglandin $E_1$, a.k.a. alprostadil), and vasodilators (e.g., papaverine).

According to various embodiments, the patient is treated by inhibiting excitement of sympathetic input to the penis. In this case, relatively high-frequency electrical stimulation (e.g., greater than about 50–100 Hz) is likely to produce such inhibition. Substances that may also or instead be used to decrease sympathetic activation include neurotransmitters and medications such as GABA, an inhibitory neurotransmitter, and/or norepinephrine antagonists (i.e., adrenergic-blocking medications) such as the alpha-adrenergic receptor blocking agent phentolamine.

Additional or alternative substances that may be infused to any of the above-named nerves, tissues, and/or blood vessels include vasodilator agents that elevate cyclic nucleotides in penile cavernosal smooth muscle, including vasoactive intestinal polypeptide (VIP) and $PGE_1$, as well as sildenafil, vardenafil, and/or other agent(s) that inhibit Phosphodiesterase type 5 (PDE5) or otherwise inhibit degradation of guanosine 3',5'-cyclic monophosphate (a.k.a., cyclic GMP or cGMP). Substances may also or instead include other substances known to result in an erectile response, such as one or more of acetylcholine, nitric oxide (NO), analogs of nitric oxide, guanylyl cyclase NO receptor agonists, and cGMP. Therapeutic substances may include traditional agents used in intracavernosal injection therapy or other therapy for erectile dysfunction, including alprostadil, papaverine, phentolamine, and androgens, such as testosterone and dihydrotestosterone (DHT). Therapeutic substances may also include genes or gene products that lead to an improvement in erectile response.

For example, SCU 160 may contain an infusion pump that releases NO using materials that slowly release NO gas, such as recently developed polymers containing derivatized silica particles that slowly release NO gas. In such embodiments, the infusion pump may draw interstitial fluid from surrounding tissue or from a source catheter or inlet, and when SCU 160 is activated to produce an erection, it runs this interstitial fluid over a surface that releases NO and delivers the fluid containing NO to, for instance, one or both corpus cavernosa 116, via a delivery catheter/infusion outlet. In such embodiments, a source catheter/inlet and a delivery catheter/outlet may be the same or different. Additionally, SCU 160 may have a fluid (e.g., saline) reservoir, and the fluid from this reservoir may be passed over the surface that releases NO and to the stimulation target. The surface that releases NO may be a part of the delivery catheter/infusion outlet, or these items may be separate.

In yet another alternative, placement of electrodes 172/172' and/or infusion outlet(s) 182/182' may be chosen to effect emission (discharge of semen) or ejaculation (ejection of semen in orgasm). While parasympathetic input is responsible for erection, sympathetic impulses are required for ejaculation. As stated earlier, the sympathetic nervous system originates in the thoracic and lumbar regions of the spinal cord. It is believed that a portion of the sympathetic outflow leaving the spinal cord at the first and second lumbar segments travels through the lower lumbar or pelvic parts of the sympathetic trunk, then via the inferior hypogastric plexus, to arrive at the vas deferens, the seminal vesicles, and the prostate. Therefore, stimulating certain branches of the inferior hypogastric plexus that innervate the prostate, seminal vesicles, and vas deferens may lead to emission and/or ejaculation. Alternatively or additionally, stimulation of the pelvic splanchnic nerves leading to the prostate may cause emission and/or ejaculation.

Furthermore, sensing means described earlier may be used to orchestrate first the stimulation of nerves that cause erection, and then, when appropriate, the stimulation of nerves that cause ejaculation. Alternatively, this orchestration may be programmed, and not based on a sensed condition.

While the invention herein disclosed has been described by means of specific embodiments and applications thereof, numerous modifications and variations could be made thereto by those skilled in the art without departing from the scope of the invention set forth in the claims. For instance, the methods and systems described herein may benefit patients who have not undergone prostatic surgery. In such cases, the electrode portion and/or infusion outlet of any leads/catheters and/or microstimulator SCU(s) would be implanted in one or more of the areas described above. If desired, the response to stimulation may be determined prior to full implantation of the system, as described above. In anther alternative, patients may choose to keep SCU external, with lead(s) and/or catheter(s) providing stimulation percutaneously.

What is claimed is:

1. A method for treating a prostatic surgery patient comprising:

providing at least one of a lead and a catheter, wherein the lead includes at least one stimulating electrode at a distal portion of the lead and the catheter includes at least one infusion outlet at a distal portion of the catheter;

during prostate surgery, implanting the distal portion of at least one of the lead and the catheter adjacent to tissue affecting the penis;

after prostate surgery, applying stimulation via at least one of the lead and the catheter to determine if a patient with erectile dysfunction is responsive to stimulation to promote erection;

operably connecting at least one system control unit to a proximal portion of at least one of the lead and the catheter for patients responsive to stimulation;

providing operating power to the at least one system control unit;

providing stimulation parameters to the at least one system control unit;

generating stimulation pulses in accordance with the stimulation parameters; and delivering the stimulation pulses via at least one of the lead and the catheter to the tissue affecting the penis.

2. The method of claim 1 wherein the tissue affecting the penis supplies parasympathetic input that promotes erection.

3. The method of claim 2 wherein the tissue affecting the penis comprises at least one nerve of the cavernous nerves, the prostatic plexus, branches of the prostatic plexus, the pelvic splanchnic nerves, and the second, third, and fourth sacral nerves.

4. The method of claim 3 wherein the stimulation pulses are electrical pulses provided at less than about 50 to 100 Hz.

5. The method of claim 3 wherein the stimulation pulses are infusion pulses providing at least one of an excitatory drug, acetylcholine and an acetylcholine agonist.

6. The method of claim 1 wherein the tissue affecting the penis supplies sympathetic input inhibiting erection.

7. The method of claim 6 wherein the tissue affecting the penis comprises one or more of the sympathetic ganglia from which the hypogastric nerves arise, the hypogastric nerves, the nerves of the inferior hypogastric plexus, and the nerves of the branches of the inferior hypogastric plexus.

8. The method of claim 7 wherein the stimulation pulses are electrical pulses provided at greater than about 50 to 100 Hz.

9. The method of claim 7 wherein the stimulation pulses are infusion pulses providing at least one of an inhibitory drug, GABA, phentolamine, and a norepinephrine antagonist.

10. The method of claim 1 wherein the tissue affecting the penis comprises at least one of the corpus cavernosa, corpus spongiosum, cavernous nerves, nerves of the prostatic plexus, branches of the prostatic plexus, pelvic splanchnic nerves, second, third, and fourth sacral nerves, sympathetic ganglia from which the hypogastric nerves arise, hypogastric nerves, nerves of the inferior hypogastric plexus, branches of the inferior hypogastric plexus, branches of the inferior hypogastric plexus that innervate at least one of the prostate, seminal vesicles, and vas deferens, pelvic splanchnic nerves leading to the prostate, blood vessels supplying the penis, blood vessels draining the penis, internal iliac arteries, internal pudendal arteries, dorsal arteries of the penis, deep arteries of the penis, the deep dorsal vein of the penis, and the urethra.

11. The method of claim 10 wherein the stimulation pulses are infusion pulses providing at least one of a drug that elevates cyclic nucleotides in penile cavernosal smooth muscle, a drug that inhibits PDE5, a drug that inhibits degradation of cGMP, vasoactive intestinal polypeptide, prostaglandin $E_1$, sildenafil, vardenafil, cGMP, acetylcholine, nitric oxide, analogs of nitric oxide, a guanylyl cyclase nitric oxide receptor agonist, papaverine, phentolamine, an androgen, a gene that leads to improved erectile response, and a gene product that leads to improved erectile response.

12. The method of claim 1 wherein the tissue affecting the penis affects emission or ejaculation.

13. The method of claim 12 wherein the tissue affecting the penis comprises at least one nerve of the branches of the inferior hypogastric plexus that innervate at least one of the prostate, seminal vesicles, and vas deferens.

14. The method of claim 12 wherein the at least one nerve comprises at least one of the pelvic splanchnic nerves leading to the prostate.

15. The method of claim 12 wherein the stimulation pulses are electrical pulses provided at less than about 50 to 100 Hz.

16. The method of claim 12 wherein the stimulation pulses are infusion pulses providing at least one of acetylcholine and an acetylcholine agonist.

17. The method of claim 1 further comprising sensing a condition of the patient with at least one sensor and using the sensed condition to adjust the stimulation parameters of at least one system control unit.

18. The method of claim 17 wherein the at least one sensor senses at least one of nerve activity, muscle activity, electrical activity of the brain, penile arteriole pressure, pressure in corpus cavemosum, pressure in corpus spongiosum, joint angle, tumescence, impedance, a neurotransmitter, a neurotransmitter breakdown product, a drug, a medication, a hormone, a ketone, an electrolyte, an enzyme, an interleukin, a substances in the blood plasma, and a substance in the local interstitial fluid.

19. The method of claim 1 further comprising providing more than one system control unit.

20. A method for treating a prostatic surgery patient comprising:

providing at least one microstimulator for delivering stimulation to tissue;

during prostate surgery, implanting the at least one microstimulator adjacent to tissue affecting the penis;

applying stimulation via at least one microstimulator to determine if a patient with erectile dysfunction is responsive to stimulation to promote erection;

providing operating power to the at least one microstimulator of patients responsive to stimulation;

providing stimulation parameters to the at least one microstimulator of patients responsive to stimulation;

generating stimulation pulses in accordance with the stimulation parameters; and delivering the stimulation pulses to the tissue affecting the penis.

21. The method of claim 20 wherein the at least one microstimulator is leadless.

22. The method of claim 20 wherein the at least one microstimulator includes at least one of a lead and a catheter.

23. A system for treating a prostatic surgery patient comprising:

at least one of a lead and a catheter, the lead including at least one stimulating electrode at a distal portion and the catheter including at least one infusion outlet at a distal portion;

means for implanting during prostate surgery the distal portion of at least one of the lead and the catheter adjacent to tissue affecting the penis;

an external stimulator configured for connection to a proximal portion of at least one of the lead and the catheter, and configured to apply stimulation through at least one of the lead and the catheter to determine if a patient with erectile dysfunction after prostate surgery is responsive to stimulation to promote erection;

at least one implantable system control unit configured for connection to the proximal portion of at least one of the lead and the catheter, and configured to apply stimulation through at least one of the lead and the catheter to patients responsive to stimulation;

means for providing operating power to the at least one system control unit;

means for providing stimulation parameters to the at least one system control unit; and means for generating stimulation pulses in accordance with the stimulation parameters;

wherein at least one of the electrode and the infusion outlet deliver the stimulation pulses through at least one of the lead and catheter to the tissue affecting the penis.

24. A method for treating erectile dysfunction, comprising:

implanting at least one infusion outlet of a stimulator adjacent to a tissue affecting the penis;

infusing at least one drug to the tissue affecting the penis via the at least one infusion outlet;

wherein the at least one drug comprises at least one of a drug that elevates cyclic nucleotides in penile cavernosal smooth muscle, a drug that inhibits PDE5, a drug that inhibits degradation of cGMP, a gene that leads to improved erectile response, and a gene product that leads to improved erectile response.

25. The method of claim 24, wherein the at least one drug comprises at least one of vasoactive intestinal polypeptide, prostaglandin $E_1$, sildenafil, vardenafil, cGMP, acetylcholine, an acetylcholine agonist, nitric oxide, analogs of nitric oxide, a guanylyl cyclase nitric oxide receptor agonist, papaverine, GABA, phentolamine, an androgen, and a norepinephrine antagonist.

26. The method of claim 24 wherein the tissue affecting the penis comprises at least one of the corpus cavernosa, corpus spongiosum, cavernous nerves, nerves of the prostatic plexus, branches of the prostatic plexus, pelvic splanchnic nerves, second, third, and fourth sacral nerves, sympathetic ganglia from which the hypogastric nerves arise, hypogastric nerves, nerves of the inferior hypogastric plexus, branches of the inferior hypogastric plexus, branches of the inferior hypogastric plexus that innervate at least one of the prostate, seminal vesicles, and vas deferens, pelvic splanchnic nerves leading to the prostate, blood vessels supplying the penis, blood vessels draining the penis, internal iliac arteries, internal pudendal arteries, dorsal arteries of the penis, deep arteries of the penis, the deep dorsal vein of the penis, and the urethra.

* * * * *